United States Patent [19]
Yu et al.

[11] Patent Number: 5,801,260
[45] Date of Patent: Sep. 1, 1998

[54] CARBONOTHIOATE PHOSPHOLIPID ANALOGS AS SUBSTRATE OF PHOSPHOLIPASES AND LIPASES

[75] Inventors: Lin Yu, San Diego; Robert John Termansky, Carlsbad, both of Calif.

[73] Assignee: LaJolla Pharmaceuticals Co., San Diego, Calif.

[21] Appl. No.: 476,258

[22] Filed: Jun. 7, 1995

[51] Int. Cl.$^6$ ................................................. C07F 9/02
[52] U.S. Cl. ........................ 554/81; 584/78; 584/79; 584/82; 584/101; 584/102; 584/114; 568/61; 568/62; 568/63; 568/579; 568/583; 568/589; 568/700; 568/704; 568/852
[58] Field of Search ........................ 554/78, 79, 82, 554/107, 102, 114; 568/61, 62, 63, 579, 583, 589, 700, 704, 852

[56] References Cited

U.S. PATENT DOCUMENTS 5,277,508  1/1994  Kozikowski et al. ................. 558/155

OTHER PUBLICATIONS

Dennis, E.A., "Phospholipases" *The Enzymes* 1983, 3rd. Ed., Academic Press, New York, 16, 307–353.

Irvine, R.F., "How is the level of free arachidonic acid controlled in mammalian cells?" *Biochem J.* 1982, 204, 3–16.

Snyder, F., "Chemical and biochemical aspects of platelet activating factor: A novel class of acetylated ether–linked choline–phospholipids" *Med. Res. Rev.* 1985, 5, 107–140.

Pruzanski, W. & Vadas, P., "Phospholipase $A_2$—a mediator between proximal and distal effectors of inflammation" *Immunology Today* 1991, 12, 143–146.

Vadas, P. & Pruzanski, W., "Biology of disease: Role of secretory phospholipases $A_2$ in the pathobiology of disease" *Lab. Invest.* 1986, 55, 391–404.

Nevalainen, T.J., "Serum phospholipases $A_2$ in inflammatory diseases" *Clin. Chem.* 1993, 39, 2453–2459.

Green, J.-A., et al., "Circulating phospholipase $A_2$ activity associated with sepsis and septic shock is indistinguishable from that associated with rheumatoid arthritis" *Inflammation*, 1991, 15, 355–367.

Vadas, P., et al., "Serum phospholipase $A_2$ enzyme activity and immunoreactivity in a prospective analysis of patients with septic shock" *Life Sci.* 1992, 50, 807–811.

Nevalainen, T.J., "Phospholipase $A_2$ in acute pancreatitis" *Scand. J. Gastroenterol.* 1988, 23, 897–904.

Smith, G.M., et al., "Measurement of human phospholipase $A_2$ in arthritis plasma using a newly developed sandwich ELISA" *British J. Rheumatology* 1992, 31, 175–178.

Dole, V.P., "A relation between non–esterified fatty acids in plasma and the metabolism of glucose" *J. Clin. Invest.* 1956, 35, 150–154.

van den Bosch, H., et al., "Phospholipase $A_2$ from rat liver mitochondria" *Methods Enzymol.* 1991, 197, 365–373.

Lister, M.D., et al., "Kinetic analysis of the $CA^{2+}$–dependent, membrane–bound, macrophage phospholipase $A_2$ and the effects of arachidonic acid" *J. Biol. Chem.* 1988, 263, 7506–7513.

Kramer, R.M. & Pepinsky, R.B., "Assay and purification of phospholipase $A_2$ from human synovial fluid in rheumatoid arthritis" *Methods Enzymol.* 1991, 197, 373–381.

Yu, L. & Dennis, E.A., "Thio–based phospholipase assay" *Methods Enzymol.* 1991, 197, 65–75.

Reynolds, L.J., et al., "Analysis of human synovial fluid phospholipase $A_2$ on short chain phosphatidylcholine–mixed micelles: Development of a spectrophotometric assay suitable for a microtiterplate reader" *Anal. Biochem.* 1992, 204, 190–197.

(List continued on next page.)

*Primary Examiner*—Gary Geist
*Assistant Examiner*—Deborah D. Carr
*Attorney, Agent, or Firm*—Morrison & Foerster, LLP

[57] ABSTRACT

Novel substrates of phospholipases, lysophospholipases and lipases are disclosed.

2 Claims, 9 Drawing Sheets

OTHER PUBLICATIONS

Reynolds, L.J., et al., "1-hexadecyl-2-arachidonoylthio-2-deoxy-sn-glycero-3- phosphorylcholine as a substrate for the microtiterplate assay of human cytosolic phospholipase $A_2$," *Anal. Biochem.* 1994, 217, 25–32.

Hendrickson, H.S., et al., "Synthesis of a naphthylvinyl-labeled glycerol ether analog of phosphatidylcholine and its use in the assay of phospholipase $A_2$," *J. Lipid Res.* 1987, 28, 864–872.

Radvanyi, F., et al., "A sensitive and continuous fluorometric assay for phospholipase $A_2$ using pyrene-labeled phospholipids in the presence of serum albumin" *Anal. Biochem.* 1989, 177, 103–109.

Hendrickson, H.S., "Fluorescence–based assays of lipases, phospholipases, and other lipolytic enzymes" *Anal. Biochem.* 1994, 219, 1–8.

Hendrickson, H.S. & Hendrickson, E.K., "A facile asymmetric synthesis of glycerol phospholipids via tritylglycidol prepared by the asymmetric epoxidation of allyl alcohol. Thiolester and thioether analogs of phosphatidylcholine" *Chem. Phys. Lipids* 1990, 53, 115–120.

Satouchi, K., et al., "Evidence for production of 1-acyl-2-acetyl-sn-glyceryl-3-phosphorylcholine concomitantly with platelet–activating factor" *Biochem. Biophys. Res. Comm.* 1985, 128, 1409–1417.

Washburn, W.N. & Dennis, E.A., "Suicide–inhibitory bifunctionally linked substrates (SIBLINKS) as phospholipase $A_2$ inhibitors" *J. Biol. Chem.* 1991, 266, 5042–5048.

Tegeler et al., "Hydroxy–, alkoxy–, and benzyloxy–substituted phospholipids, a process for their preparation, their pharmaceutical compositions, and their use as phospholipase A2 inhibitors" *Chem. Abstracts* (1989) 111(5):576 (abstract No. 39106z).

Campbell et al., "Synthesis of structural variants of phospholipids: inhibition of phospholipase A2" *Chem. Abstracts* (1990) 112(15):781 (abstract No. 39698h).

AMIDE ANALOGUE

SIBLINKS

CARBONOTHIOATE PHOSPHOLIPID ANALOGS AS SUBSTRATE OF PHOSPHOLIPASES AND LIPASES

TECHNICAL FIELD

This invention relates to chemical compounds that are novel substrates of phospholipases, lysophospholipases and lipases.

BACKGROUND

Phospholipase $A_2$ ($PLA_2$) is a hydrolytic enzyme that specifically cleaves the ester bond at the sn-2 position of phospholipids (Dennis, E. A. in *The Enzymes* 1983, 3rd. Ed., Academic Press, New York, 16, 307–353). This reaction produces a fatty acid and a lysophospholipid, which are precursors of inflammatory mediates, such as eicosanoids and platelet activating factor (Irvine, R. F. *Biochem. J.* 1982, 204, 3–16; Snyder, F. *Med. Res. Rev.* 1985, 5, 107). The role of $PLA_2$ in inflammatory disease has been proposed (Pruzanski, W. & Vadas, P. *Immunology Today* 1991, 12, 143–146; Vadas, P. & Pruzanski, W. *Lab. Invest.* 1986, 55, 391–404; Nevalainen, T. J. *Clin. Chem.* 1993, 39, 2453–2459). It is of special note that the level of $PLA_2$ is often found to be elevated in patients suffering from certain inflammatory disorders, such as sepsis and septic shock (Green, J. A., et al. *Inflammation*, 1991, 15, 355–67; Vadas, P., et al., *Life Sci.* 1992, 50, 807–811, acute pancreatitis (Nevalainen, T. J. *Scand. J. Gastroenterol.* 1988, 23, 897–904), and rheumatoid arthritis (Smith, G. M., et al. *British J. Rheumatology* 1992, 31, 175–178). These observations lead to the proposal that inhibitors of $PLA_2$ may serve as anti-inflammatory agents in vivo. Thus, the identification of suitable inhibitors of this enzyme is an important step in the process of defining potentially new anti-inflammatory agents. In order to facilitate the discovery process, suitable assays are required to measure enzymatic activity.

Currently, several assays are available, including radioactive assays (Dole, V. P. *J. Clin. Invest.* 1956, 35, 150; van den Bosch, H., et al. *Methods Enzymol.* 1991, 197, 365–373; Lister, M. D., et al. *J. Biol. Chem.* 1988, 263, 7506; Kramer, R. M. & Pepinsky, R. B. *Methods Enzymol.* 1991, 197, 373–381), the thio assay (Yu, L. & Dennis, E. A. *Methods Enzymol.* 1991, 197, 65–75; Reynolds, L. J., et al. *Anal. Biochem.* 1992, 204, 190–197; Reynolds, L. J., et al. *Anal. Biochem.* 1994, 217, 25–32) and the fluorometric assay (Hendrickson, H. S., et al. *J. Lipid Res.* 1987, 28, 864; Radvanyl, F., et al. *Anal. Biochem.* 1989, 177, 103; Hendrickson, H. S. *Anal. Biochem.* 1994, 219, 1–8). Among these assays, the thio assay is the most convenient and can be easily automated (Reynolds, L. J., et al. *Anal. Biochem.* 1992, 204, 190–197; Reynolds, L. J., et al. *Anal. Biochem.* 1994, 217, 25–32). However, the substrates of this assay require laborious syntheses (at least 6-step synthesis) (Yu, L., *Methods Enzymol.* 1991, 197, 65–75; Reynolds, L. J., et al. *Anal. Biochem.* 1994, 217, 25–32; Hendrickson, H. S. & Hendrickson, E. K. *Chem. Phys. Lipids* 1990, 53, 115–120). This invention describes a new thio assay which utilizes a substrate readily assembled from commercial materials in a one-pot synthesis. This assay is based on the unprecedented recognition of the novel substrate described herein giving rise to the release of a readily detectable species.

SUMMARY OF THE INVENTION

Figure 1:
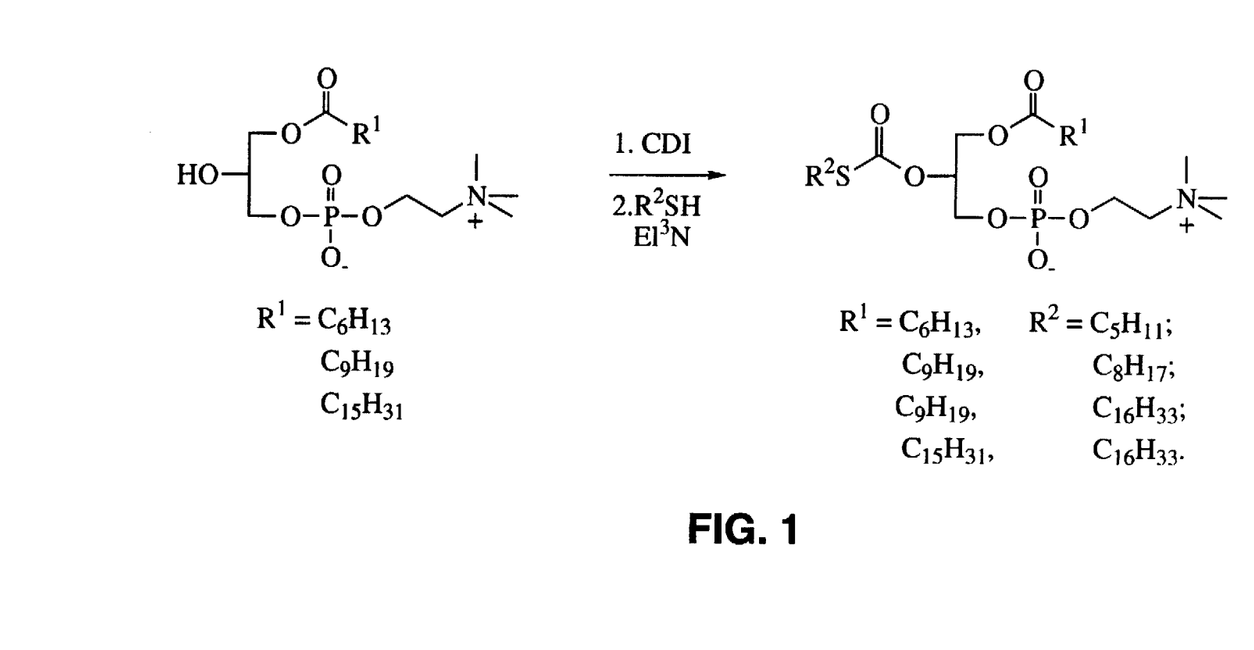
FIG. 1 shows the synthetic scheme for carbonothioate phospholipid analogs.

The present invention describes chemical compounds which are novel substrates of phospholipases, lysophospholipases and lipases. The chemical compounds of the present invention are represented by the formula:

or wherein A is oxygen, nitrogen or sulfur atom, X is a hydrogen atom, or a saturated or unsaturated alkyl or acyl group having up to 32 carbon atoms, Y is a saturated or unsaturated alkyl group having up to 32 carbon atoms, Z is a hydrogen atom, or a saturated or unsaturated alkyl or acyl group having up to 32 carbon atoms, or $-SO_3^{2-}$, or a radical of the general formula:

wherein $R^1$ is a hydroxyl group, or $-O-(CH_2)_m N^+(CH_3)_n H_{3-n}$, in which m is 2 to 4 and n is 0 to 3, or $R^1$ is an inositol, serine, glycerol, or an alkoxyl group having 1 to 4 carbons.

This invention also describes a process for producing the substrate and demonstrates their utility for the detection of enzymatic activity of phospholipases, lysophospholipases, and lipases. Preferred substrates are those wherein X is a saturated alkyl or acyl group having 6 to 16 carbons, Y is a saturated or unsaturated alkyl group having 2 to 20 carbons, and Z is a phosphoryl ester group consisting of choline, ethanolamine, inositol, serine or glycerol. Particularly preferred are substrates wherein Z is a phosphoryl ester of choline.

Figure 2:
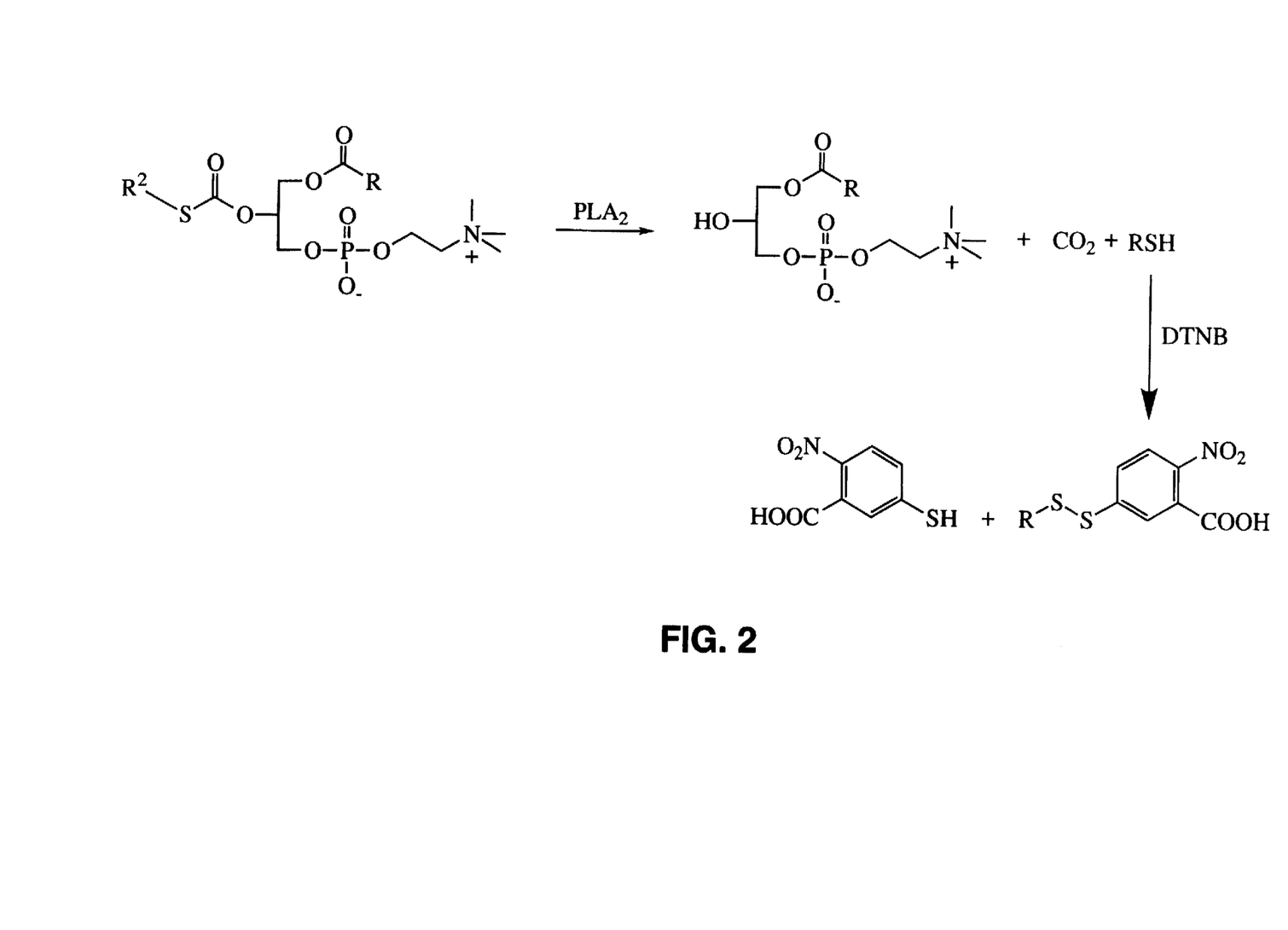
FIG. 2 shows the mechanism for the spectrophotometric determination of phospholipase $A_2$ activity using carbonothioate phospholipid analogs.

A method for the preparation of the novel substrates of the present invention is also disclosed herein. In a method within the present invention, a lysophospholipid reacts first with 1,1'-carbonyldiimidazole and then with mercaptoalkanes in the presence of triethylamine. A method for the detection of phospholipase $A_2$ is also described wherein a solution of the novel substrates of the present invention is incubated with cobra venom phospholipase $A_2$ in the presence of a thio-sensitive reagent such as 5,5'-dithio-bis(2-nitrobenzoic acid). The substrate is hydrolyzed by phospholipase $A_2$ enzyme to produce a mercaptoalkane, a lysophospholipid, and carbon dioxide. The mercaptoalkane then reacts with a thiol-sensitive reagent to produce a chromophore. The absorbance of the chromophore is measured using spectrophotometric methods.

Figure 3:
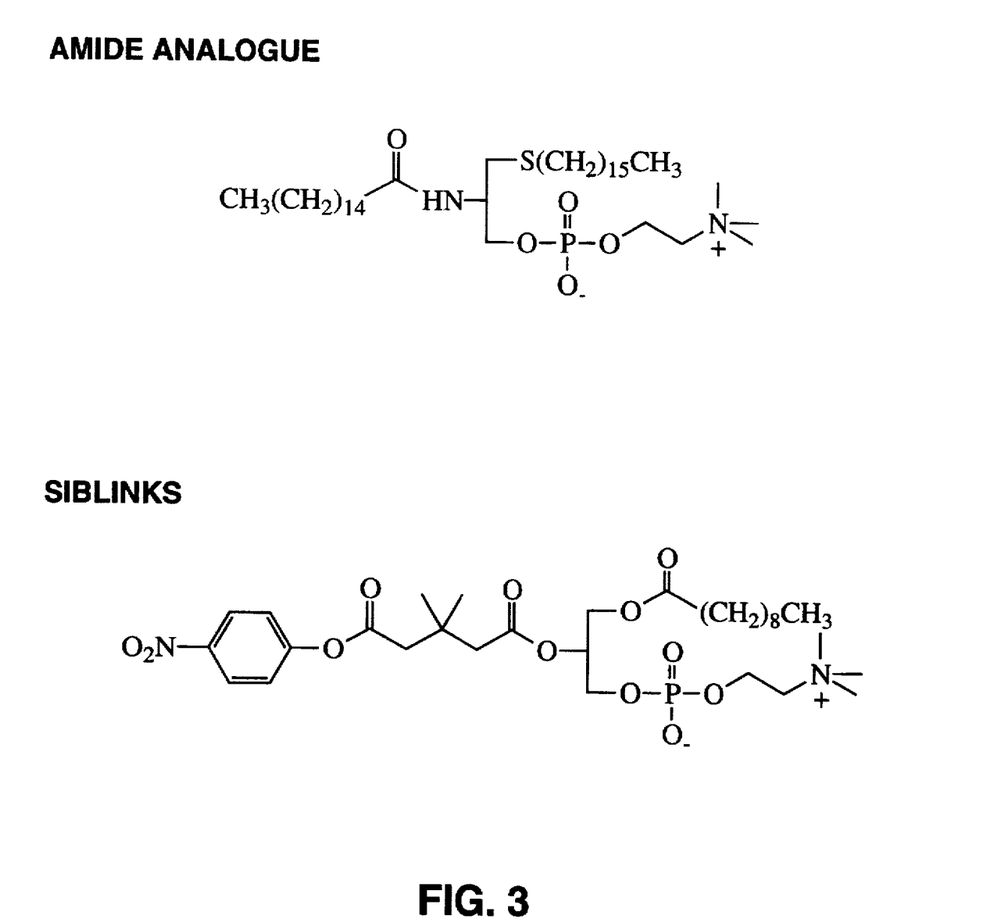
FIG. 3 shows the structures of two phospholipase $A_2$ inhibitors: the amide analog and an irreversible inhibitor.
Figure 4:
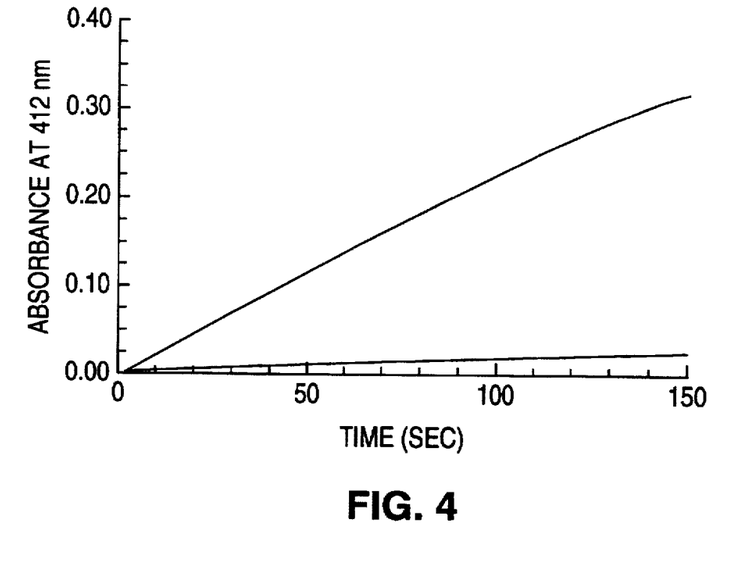
FIG. 4 shows the time course of the hydrolysis of the carbonothioate substrate catalyzed by cobra venom (Naja naja atra; cv) phospholipase $A_2$, using substrate consisting of 1-decanoyl-2-octylcarbonothioyl-sn-glycero-3-phosphocholine (0.5 mM) and Triton X-100 (4.24 mM). The assay was carried out under standard conditions (25 mM Tris-HCl (pH 8.5), 0.1 M KCl, and 10 mM $CaCl_2$) at 412 nm.
Figure 5:
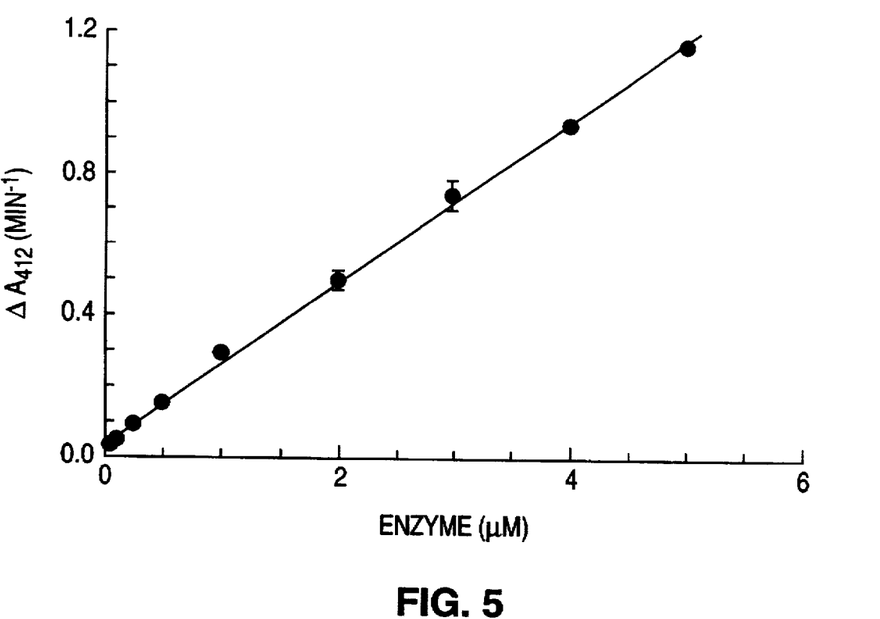
FIG. 5 shows a linear dependency of cobra venom phospholipase $A_2$ activity on the enzyme concentration in the range of 100 ng to 3,000 ng by using a substrate consisting of 1-decanoyl-2-octylcarbonothioyl-sn-glycero-3-phosphocholine (0.5 mM) and Triton X-100 (4.24 mM).
Figure 6:
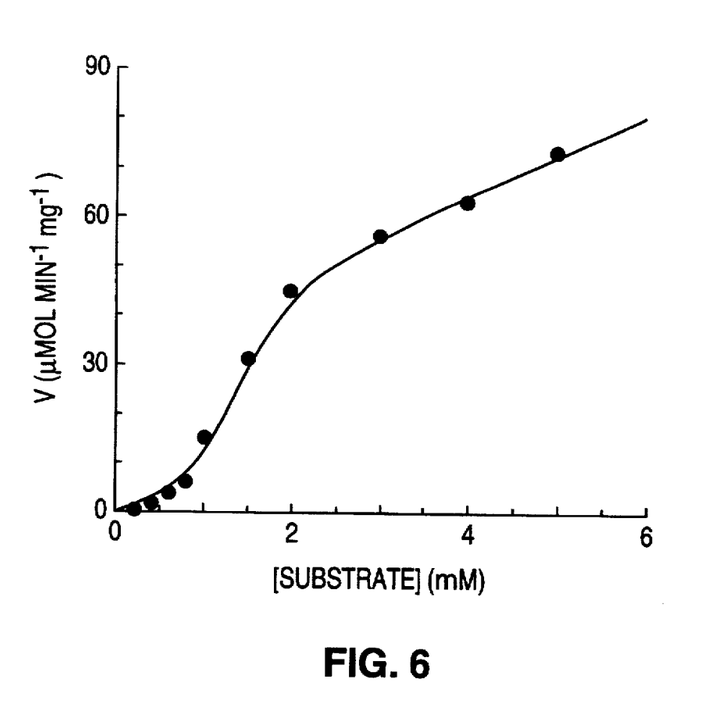
FIG. 6 shows the substrate concentration dependency of cobra venom phospholipase $A_2$ activity using 1-heptanoyl-2-pentylcarbonothioyl-sn-glycero-3-phosphocholine as substrate.
Figure 7:
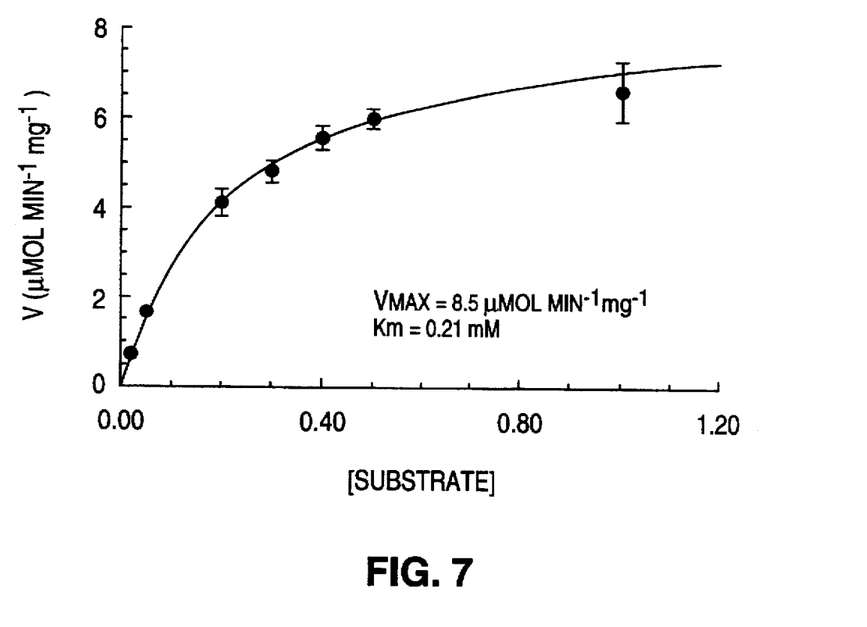
FIG. 7 shows the substrate concentration dependency of cobra venom phospholipase $A_2$ activity by using substrate consisting of 1-decanoyl-2-octylcarbonothioyl-sn-glycero-3-phosphocholine and Triton X-100. The ratio of Triton X-100/phospholipid is 8.
Figure 8:
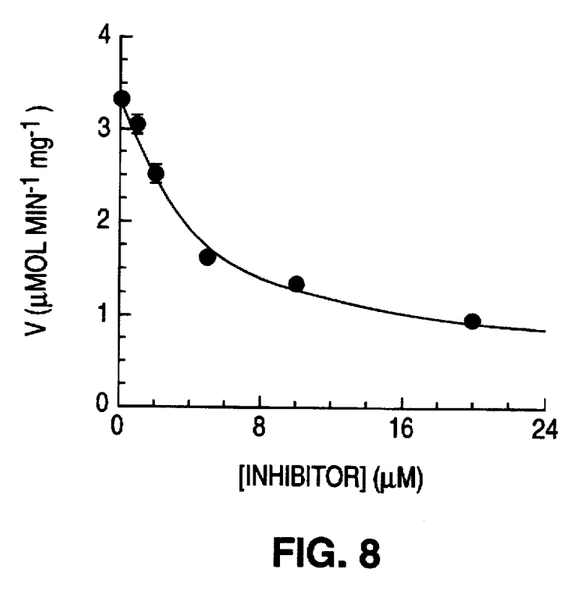
FIG. 8 shows the inhibition of cobra venom phospholipase $A_2$ by the amide substrate analogs as determined by the carbonothioate assay. The substrate used was 1-decanoyl-2-octylcarbonothioyl-sn-glycero-3-phosphocholine (0.5 mM) in the standard buffer containing 4.24 mM of Triton X-100.

A method for measuring the effectiveness of a reversible phospholipase $A_2$ inhibitor is also described wherein an enzyme inhibitor is added to a substrate solution prior to the addition of phospholipase $A_2$ enzyme. Inhibition of phospholipase $A_2$ is indicated by a decrease in absorbance reading as compared to the absorbance reading of a control without inhibitor.

Figure 9:
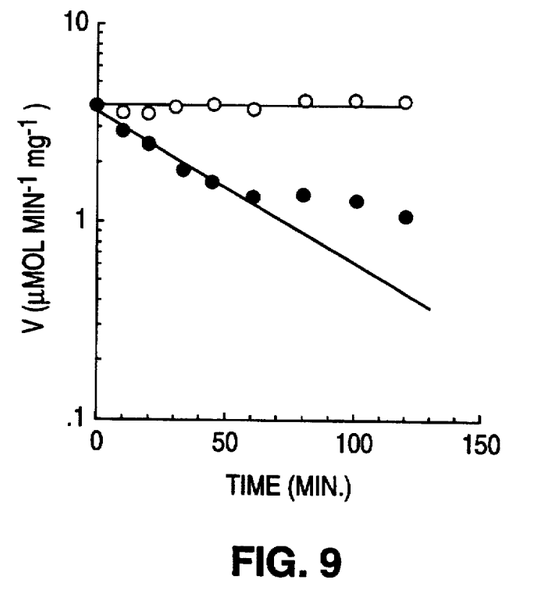
FIG. 9 shows the time-dependent inhibition of cobra venom phospholipase $A_2$ by the irreversible inhibitor in FIG. 3 as followed by the carbonothioate assay. The substrate used was 1-decanoyl-2-octylcarbonothioyl-sn-glycero-3-phosphocholine (0.5 mM) in the standard buffer containing 4.24 mM of Triton X-100.

A method for measuring the effectiveness of an irreversible phospholipase $A_2$ inhibitor is also disclosed wherein an enzyme inhibitor is first incubated with phospholipase $A_2$ enzyme. The activity of phospholipase $A_2$ enzyme is determined at various time points using methods within the present invention. Inhibition of phospholipase $A_2$ is indicated by a decrease in absorbance reading as compared to the absorbance reading of a control without inhibitor.

MODES OF CARRYING OUT THE INVENTION

EXAMPLE 1

Synthesis of 1-Heptanoyl-3-pentylcarbonothioyl-sn-glycero-3-phosphocholine (a). Preparation of 1-heptanoyl-sn-glycero-3-phosphocholine: The lysophospholipid was prepared as described (Satiycgum, K., et al. *Biochem. Biophys. Res. Comm.* 1985, 128, 1409–1417). To a solution of 1,2-diheptanoyl-sn-glycero-3-phosphocholine (1.00 g, 2.08 mmol) in 10 ml of a Tris-HCl buffer (pH 8.5), containing 25 mM Tris, 100 mM KCl, 10 mM $CaCl_2$ was added cobra venom phospholipase $A_2$ (*Naja naja atra*) (1 mg). The mixture was incubated at 40° C. for 24 hr. The solvent was evaporated off under vacuum. The residue was purified on silica gel column with $CH_2Cl_2$:MeOH:$H_2O$ (65:25:6) as eluting solvents to give a white solid (488 mg, yield 64%).

(b). Preparation of 1-Heptanoyl-3-Pentylcarbonothioyl-sn-glycero-3-phosphocholine: A solution of 1-heptanoyl-sn-glycero-3-phosphocholine (0.488 g, 1.31 mmol) and 1,1'-carbonyldiimidazole (CDI) (425 mg, 2.62 mmol) in chloroform (10 mL) was stirred at room temperature. The reaction was monitored by TLC using chloroform/methanol/water (65:25:4). After the reaction was complete (about 5 hr), mercaptopentane (273 mg, 2.62 mmol) and triethylamine (265 mg, 2.62 mmol) were added. The mixture was stirred overnight at room temperature. Then the solvent was removed under reduced pressure and the residue was purified by flash chromatography on silica gel. The column was first eluted with chloroform/methanol/water (65:25:1), followed with chloroform/methanol/water (65:25:4) to give a white solid (357 mg, 0.715 mmol, 55%). IR (neat, $cm^{-1}$) $V_{max}$ 2960, 2929, 2854, 1736, 1716, 1466, 1238, 1150, 1087, 1064, 758; $^1$H NMR (300 MHz, $CDCl_3$): δ5.28–5.32 (m, 1H) 4.31–4.38 (m, 3H), 4.21 (dd, J=12.1, 7.4, 1H), 3.99–4.03 (m, 2H), 3.84 (br s, 2H), 3.41 (s, 9H), 2.78–2.89 (m, 2H), 2.30 (t, J=7.6, 2H), 1.54–1.65 (m, 4H), 1.28–1.39 (m, 10H), 0.86–0.93 (m, 6H); $^{13}$C NMR (75 MHz, $CDCl_3$); δ173.33, 170.70, 73.81 (d, J=7.5), 66.20 (d. J=6.3), 63.41 (d, J=5.0), 62.59, 59.28 (d, J=4.6), 54.24, 34.00, 31.34, 30.99, 30.74, 29.31, 28.68, 24.69, 22.38, 22.06, 13.93, 13.83; $^{31}$P NMR (121 MHz, $CDCl_3$): δ–0.15; UV (MeOH) 204 nm (4696).

HRMS (FAB) m/e (M+1) Calcd for $C_{21}H_{43}NO_8PS$: 500.2447, obs: 500.2458.

EXAMPLE 2

Synthesis of 1-Decanoyl-2-octylcarbonothioyl-sn-glycero-3-phosphocholine

A solution of 1 decanoyl-sn-glycero-3-phosphocholine (200 mg, 0.486 mmol) and 1,1'-carbonyldiimidazole (190 mg, 1.17 mmol) in chloroform (10 mL) was stirred for two days at room temperature. Mercaptooctane (142 mg, 0.97 mmol) was added the mixture was stirred for 24 hr at room temperature. The solvent was removed under vacuum and the residue was purified by flash chromatography on silica gel. The column was first eluted with chloroform/methanol/water (65:25:1) followed with chloroform/methanol/water (65:25:3) to give a white solid (166 mg, 0.284 mmol, 59%): IR (neat, $cm^{-1}$) $V_{max}$ 2923, 2853, 1734, 1710, 1479, 1249, 1150, 1098, 1066, 968; $^1$H NMR (300 MHz, $CDCl_3$): δ5.27–5.32 (m, 1H), 4.33–4.38 (m, 3H), 4.21 (dd, J =12.1, 7.4, 1H), 3.99–4.04 (m, 2H), 3.83 (br s, 2H), 3.39 (s, 9H), 2.74–2.91 (m, 2H), 2.29 (t, J=7.6, 2H), 1.57–1.67 (m, 4H), 1.27 (br s, 22H), 0.88 (t, J=6.6, 6H); $^{13}$C NMR (75 MHz, $CDCl_3$): δ173.39, 170.75, 73.91 (d), 66.35 (d), 63.47 (d), 62.66, 59.27 (d), 54.37, 34.07, 31.83, 31.74, 31.08, 29.70, 29.40, 29.25, 29.11, 29.05, 28.74, 28.81, 22.61, 22.58, 14.04; $^{31}$P NMR (121 MHz, $CDCl_3$): δ–0.95; UV (MeOH) 206 nm (4127).

HRMS (FAB) m/e (M+1) Calcd for $C_{27}H_{55}NO_8PS$: 584.3386, obs: 584.3391.

EXAMPLE 3

Synthesis of 1-Decanoyl-2-hexadecanoylcarbonothioyl-sn-glycero-3-phosphocholine

A solution of 1-decanoyl-sn-glycero-3-phosphocholine (530 mg, 1.29 mmol) and 1,1'-carbonyldiimidazole (418 mg, 2.58 mmol) in chloroform (10 mL) was stirred at room temperature overnight. Mercaptohexadecane (666 mg, 2.58 mmol) and triethylamine (261 mg, 2.58 mmol) were added. After the mixture was stirred overnight at room temperature, the solvent was removed under vacuum. The resulting residue was purified by flash chromatography on silica gel. The column was first eluted with chloroform/methanol/water (65:25:1, followed with chloroform/methanol/water (65:25:4) to give a white solid (474 mg, 0.681 mmol, 53%): IR (neat, cm$^{-1}$) $V_{max}$ 2922, 2852, 1741, 1716, 1467, 1242, 1149, 1091, 1066, 966; $^1$H NMR (300 MHz, CDCl$_3$): δ5.28–5.32 (m, 1H), 4.32–4.38 (m, 3H), 4.21 (dd, J=12.1, 7.5, 1H), 3.99–4.03 (m,2H), 3.84 (br s, 2H), 3.40 (s, 9H), 2.79–2.89 (m, 2H), 2.28 (t, J=7.6, 2H), 1.57–1.64 (m, 4H), 1.26 (br s, 38H), 0.88 (t, J=6.7, 6H); $^{13}$C NMR (75 MHz, CDCl$_3$): δ173.34, 170.75, 73.81 (d, J=7.5), 66.24 (d, J=8.6), 63.50 (d, J=4.4), 62.69, 59.29 (d, J=4.4), 54.33, 34.08, 31.87, 31.84, 31.08, 29.73, 29.67, 29.62, 29.53, 29.42, 29.31, 29.26, 29.15, 29.12, 28.79, 24.80, 22.63, 14.06; $^{31}$P NMR (121 MHz, CDCl$_3$): δ−0.45; UV (MeOH) 206 nm (5741).

HRMS (FAB) m/e (M+1) Calcd for $C_{35}H_{71}NO8PS$: 696.4638, obs: 696.4626.

EXAMPLE 4

Synthesis of 1-Hexadecanoyl-2-hexadecylcarbonothioyl-sn-glycero-3-phosphocholine A solution of 1-hexadecanoyl-sn-glycero-3-phosphocholine (200 mg, 0.40 mmol) and 1,1'-carbonyldiimidazole (131 mg, 0.80 mmol) in chloroform (2.5 mL) was stirred at room temperature. The reaction was monitored by TLC using chloroform/methanol/water (65:25:4). After the reaction was complete (about 2 hr), mercaptohexadecane (207 mg, 0.80 mmol) and triethylamine (81 mg, 0.80 mmol) were added. The mixture was stirred overnight at room temperature. The solvent was removed under vacuum and the residue was purified by flash chromatography on silica gel. The column was first eluted with chloroform/methanol/water (65:25:1), followed with chloroform/methanol/water (65:25:3) to give a white solid (196 mg, 0.251 mmol, 62%): IR (neat, cm$^{-1}$) $V_{max}$ 22923, 2853, 1735, 1719, 1467, 1249, 1221, 1146, 1090, 1071, 759; $^1$H NMR (300 MHz, CDCl$_3$): δ5.28–5.31 (m, 1H) 4.32–4.37 (m, 3H), 4.21 (dd, J=12.1, 7.6, 1H), 4.00–4.03 (m, 2H), 3.79 (br s, 2H), 3.36 (s, 9H), 2.74–2.92 (m, 2H), 2.29 (t, J=7.6, 2H), 1.57–1.64 (m, 4H), 1.26 (br s, 50H), 0.88 (t, J=6.7, 6H); $^{13}$C NMR (75 MHz, CDCl$_3$): δ173.40, 170.77, 73.78 (d, J=7.3), 66.25 (d) 63.51 (d), 62.69, 59.39 (d), 54.35, 34.09, 31.89, 31.10, 29.69, 29.64, 29.55, 29.53, 29.33, 29.18, 28.82, 24.83, 22.64, 14.06; $^{31}$P NMR (121 MHz, CDCl$_3$): δ−0.45; UV (MeOH) 206 nm (5440).

HRMS (FAB) m/e (M+1) Calcd for $C_{41}H_{83}NO_8PS$: 780.5577, obs: 780.5554.

EXAMPLE 5

Determination of the enzymatic activity of phospholipase A$_2$ using monomeric or pure micellar substrate (a) Reagents:
Buffer A: 25 mM Tris-HCl (pH 8.5), 0.1 M KCl, 10 mM CaCl$_2$ Buffer B: 25 mM Tris-HCl (pH 8.5), 0.1 M KCl, 10 mM CaCl$_2$, 0.24 mM Triton X-100

Buffer C: 25 mM Tris-HCl (pH 8.5), 0.1 M KCl, 10 mM CaCl$_2$, 4.24 mM Triton X-100

DTNB: 50 mM 5,5'-dithiobis(2-nitrobenzoic acid) in ethanol

Carbonothioate phospholipid: 10 mM in methylene chloride (b) Method: The desired amount of carbonothioate phospholipid in methylene chloride was evaporated to dryness under a stream of nitrogen. An appropriate volume of buffer A is added. This solution was sonicated in a bath sonicator to clearness. The assay was carried out at 40° C. A cuvette, containing 0.3 mL of assay mixture and 5 μL of DTNB was placed in the compartment of a spectrophotometer thermostated at 40° C. After equilibration of the substrate for 2 min at 40° C., a stable baseline was recorded for 150 sec. To initiate the reaction, cobra venom phospholipase A$_2$ (*Naja naja atra*) (5 μL containing 125 ng protein in buffer B) was added to the cuvette and the reaction was recorded spectrophotometrically at 412 nm for 150 sec. The phospholipase activity is calculated using the extinction coefficient of 12,000 M$^{-1}$ cm$^{-1}$. Between each run, the cuvette is rinsed with Clorox, water and acetone.

EXAMPLE 6

Determination of the enzymatic activity of phospholipase A$_2$ using mixed micellar substrate Method: The appropriate volume of carbonothioate phospholipid in methylene chloride was dried under a stream of nitrogen. To prepare mixed micelles, the appropriate volume of buffer C was added, and the volume was brought to the final volume with buffer B. This solution was bath-sonicated to obtain a clear solution. The enzymatic activity was determined similarly to Example 5 except that 500 ng enzyme was used.

EXAMPLE 7

Determination of the potency of a reversible inhibitor of phospholipase A$_2$

A solution of 1-decanoyl-2-octylcarbonothioyl-sn-glycero-3-phosphocholine (1.0 mM) in buffer C was prepared as in Example 6. A solution of an amide analog (40 μM), 1-hexadecyl-thio-2-hexadecanoylamino-1,2-dideoxy-sn-glycero-3-phosphocholine, in buffer C was also prepared as in Example 6. Aliquots of these two solutions plus buffer C were combined to obtain the proper concentration of the inhibitor in the micelles. The final assay contained 0.5 mM carbonothioate phospholipid substrate and various concentrations of the amide analog (from 1 μM to 20 μM) in buffer C. The enzymatic activity in the presence of the amide analog was determined as in Example 6.

EXAMPLE 8

Determination of the potency of an irreversible inhibitor of phospholipase A$_2$ The study of PLA$_2$ inactivation by an irreverisble inhibitor was carried out by incubating the enzyme (10 μg/ml) at 40° C. in 5 mM Tris-HCl (pH 8.0), 10 mM CaCl$_2$, and 100 mM KCl with 100 μM of an irreversible inhibitor (SIBLINKS) in sonicated vesicles, which was prepared as described (Washburn, W. N. & Dennis, E. A. *J. Biol. Chem.* 266, 5042–5048 (1991)). Aliquots (50 μL) were removed at various time points and tested at 40° C. for the residual activity. The substrate used was 1-decanoyl-2-octylcarbonothioyl-sn-glycero-3-phosphocholine (0.6 mM), which was co-micellized with Triton X-100 (2.55 mM) in buffer A. The residual activity was measured similarly to Example 6. For each assay, 0.25 mL of the substrate solution and 5 μL of DTNB were used. The reaction was initiated with preincubated phospholipase $A_2$ (*Naja naja atra*) (50 μL containing 500 ng protein). The final concentration of the substrate and Triton X-100 are 0.5 mM and 4.25 mM, respectively.

We claim:

1. A phospholipase and lipase substrate having the general formula:

or wherein

A is oxygen, nitrogen or sulfur atom,

X is at least one hydrogen atom, or a saturated or unsaturated alkyl or acyl group having up to 32 carbon atoms, Y is a saturated or unsaturated alkyl group having up to 32 carbon atoms, Z is a phosphoryl ester of choline.

2. A method for producing the substrate of claim 1 comprising the steps of:

(a) reacting a lysophospholipid with 1,1'-carbonyldiimidazole;

(b) reacting the product of step (a) with a mercaptoalkane in the presence of triethylamine.

* * * * *